(12) United States Patent
Arturi

(10) Patent No.: US 9,504,419 B2
(45) Date of Patent: Nov. 29, 2016

(54) MALE CHASTITY DEVICE HAVING A SENSOR FOR DETECTING PROHIBITED BEHAVIORS

(76) Inventor: Iro Arturi, Southport (AU)

( * ) Notice: Subject to any disclaimer, the term of this patent is extended or adjusted under 35 U.S.C. 154(b) by 1102 days.

(21) Appl. No.: 13/115,882

(22) Filed: May 25, 2011

(65) Prior Publication Data

US 2011/0295156 A1    Dec. 1, 2011

(51) Int. Cl.
| | | |
|---|---|---|
| A61B 5/00 | (2006.01) | |
| A61N 1/22 | (2006.01) | |
| A61N 1/32 | (2006.01) | |
| A61N 1/36 | (2006.01) | |
| A61H 19/00 | (2006.01) | |

(52) U.S. Cl.
CPC .............. *A61B 5/4393* (2013.01); *A61N 1/22* (2013.01); *A61N 1/321* (2013.01); *A61N 1/36007* (2013.01); *A61B 5/6802* (2013.01); *A61B 5/6813* (2013.01); *A61B 5/7267* (2013.01); *A61H 19/32* (2013.01); *A61H 2201/5015* (2013.01); *A61H 2201/5061* (2013.01); *A61H 2201/5092* (2013.01); *A61H 2230/505* (2013.01); *A61H 2230/655* (2013.01)

(58) Field of Classification Search
CPC .......... A61F 5/00; A61F 5/0096; A61F 5/41; A61F 2005/414; A61F 2005/417; A61F 2005/418; A61F 6/00; A61F 6/02; A61F 6/04; A61H 19/30; A61H 19/32; A61B 5/4393; A61B 5/6802; A61B 5/6813; A61B 5/7267; A61N 1/22; A61N 1/321; A61N 1/36007
USPC ............ 128/846, 869, 870, 883; 600/39, 41, 600/300, 301, 372, 382, 384, 557, 587
See application file for complete search history.

(56) References Cited

U.S. PATENT DOCUMENTS

| | | | | |
|---|---|---|---|---|
| 396,212 | A * | 1/1889 | Long ..................... | A61F 5/0096 128/883 |
| 4,977,906 | A * | 12/1990 | Di Scipio ..................... | 128/885 |
| 7,578,296 | B2 * | 8/2009 | Miller ................... | A61F 5/0096 128/883 |
| 8,000,792 | B1 * | 8/2011 | Dechev et al. ................. | 607/41 |
| 8,007,431 | B2 * | 8/2011 | Miller et al. .................... | 600/39 |
| 8,403,865 | B2 * | 3/2013 | Halperin et al. .............. | 600/584 |
| 8,505,543 | B2 * | 8/2013 | Miller ........................... | 128/883 |
| 8,607,799 | B1 * | 12/2013 | Ma ................................. | 128/883 |
| 8,731,646 | B2 * | 5/2014 | Halperin et al. .............. | 600/509 |
| 2006/0106291 | A1 * | 5/2006 | Sidelnik et al. .............. | 600/300 |
| 2006/0241510 | A1 * | 10/2006 | Halperin et al. .............. | 600/534 |
| 2010/0089406 | A1 * | 4/2010 | Kachiguina ................... | 128/842 |
| 2010/0160882 | A1 * | 6/2010 | Lowe ............................ | 604/361 |
| 2010/0200004 | A1 * | 8/2010 | Miller ........................... | 128/883 |
| 2014/0171767 | A1 * | 6/2014 | Hotaling ...................... | 600/323 |

* cited by examiner

Primary Examiner — Kari Petrik
Assistant Examiner — Raymond E Harris
(74) Attorney, Agent, or Firm — Russ Weinzimmer & Associates, PC

(57) ABSTRACT

A male chastity device utilizes sensors to detect sexual arousal, sexual activity, and/or attempts to tamper with or remove the device. It reports sensed data and/or employs an aversive electric stimulus to discourage the detected unwanted behaviors. The male chastity apparatus includes a structural element wearable on male genital anatomy, and at least one sensor for detecting unwanted activity relating to the male genital anatomy. The apparatus can also include at least two electrodes capable of delivering aversive stimulation to the male genital anatomy. The at least two electrodes can also be capable of delivering pleasurable stimulation to the male genital anatomy. The structural element can also include electrodes for electrically preventing or electrically inhibiting removal of the structural element from the male anatomy.

2 Claims, 12 Drawing Sheets

MALE CHASTITY DEVICE HAVING A SENSOR FOR DETECTING PROHIBITED BEHAVIORS

CROSS-REFERENCES TO RELATED APPLICATIONS

This application receives priority from the Provisional patent application Ser. No. 61/348,691, entitled "Male Chastity Devices and Improvements Thereto", filed May 26, 2010 incorporated herein by reference in its entirety.

FIELD OF THE INVENTION

This invention relates to chastity devices, and more particularly to male chastity devices.

BACKGROUND

Chastity devices have a long history, some forms of them dating back millennia. A male chastity device is installed and locked onto a man's genitals, with the key or code for unlocking it typically being under the control of the man's sexual partner. This ensures that the man engages in sexual activity only with the key holder. Male chastity devices, at least effective ones, have proven to be difficult to create given the external nature of male genitalia. Prior art chastity devices have often proven to be wildly complicated, requiring belts, straps, harnesses, and/or rigid pants and suspenders. They often require large, awkward attachments to the penis and testicles, making them cumbersome and uncomfortable for the user. Further complications are due to the need to provide an outlet for urination. More recently, smaller male chastity systems made of lighter materials have appeared. Among these are the popular plastic CB line (for instance the CB6000) by AL Enterprises (U.S. Pat. No. 7,578,296), silicone devices such as BirdLock and the BON4, and devices with radically different construction such as the various plastic Exobelt models. These devices are more comfortable than their antique, steel counterparts. However many issues remain concerning their security and comfort. Users report discomfort from hard materials, skin abrasion from seams in the silicone housings, lack of proper blood circulation, and ease of extraction of the penis. Essentially, when the device is tight enough to be secure, it is not tight enough to be comfortable and permit proper blood circulation. When it is loose enough to allow some degree of comfort and circulation, there is very little security.

SUMMARY OF THE INVENTION

The male chastity device performs these key functions:
a. Sensing wearer states and actions by means of sensors. Said states may also be recorded, reported, and/or actively deterred
b. Optionally delivering an uncomfortable electrical stimuli, such as a current pulse, or denying pleasurable stimuli, so as to discourage unwanted and/or prohibited behaviors The main benefits of introducing these functions are the increased security and the possibility to increase comfort by doing away with traditional constrictive, "no access" configurations of chastity devices. In some embodiments, the housing of the chastity device, as described and claimed herein, contains the penis, and can be loose enough to be comfortable (in which case security is achieved with the "anti pullout" measures described). In other embodiments, there is no housing, in the case of the "cageless" embodiments. Realizing that securely preventing access to the penis—an organ of variable size, rigidity and shape—requires a degree of compression that is not compatible with comfort and health, the present invention does not seek to completely prevent access via solely mechanical means, but additionally or instead, detects and possibly also reports extraction to an interested authority (such as the wearer's partner or "keyholder"). Additionally, this device is able to automatically provide a deterrent to extraction, i.e., electrical stimulation and/or arousal, that will accomplish essentially the same thing, but more reliably, more safely, more practically, and more comfortably for long-term wear.

One general aspect of the invention is a male chastity apparatus including: a structural element wearable on male genital anatomy; and at least one sensor for detecting unwanted activity relating to the male genital anatomy.

In some embodiments, the unwanted activity is at least one of: an attempt to achieve sexual arousal; an attempt to leave a designated area; touching the male genital anatomy; an erection of the male genital anatomy; motions of the male genital anatomy associated with erotic arousal; and intercourse involving the male genital anatomy.

In some embodiments, the apparatus further includes: a device for recording and/or reporting signals from the at least one sensor regarding detection of unwanted activity relating to the male genital anatomy.

In some embodiments, the unwanted activity is removal of the structural element from the male genital anatomy.

In some embodiments, the structural element is structured so as to mechanically prevent removal of the structural element from the male anatomy.

In some embodiments, the structural element includes electrodes for electrically preventing or electrically inhibiting removal of the structural element from the male anatomy.

In some embodiments, the at least one sensor is one of: An accelerometer; A current change sensor; A resistance change sensor; A temperature change sensor; An optical sensor; An infra-red sensor; A pressure change sensor; A presence/absence sensor; A Perimeter sensor; A Location sensor; A Distance sensor; A capacitive sensor; An ultra-sonic sensor; An optoelectronic sensor; A force sensing resistor; A strain gauge; A thermistor; and A piezoelectric sensor.

In some embodiments, the apparatus further includes at least two electrodes capable of delivering at least one of: aversive stimulation to the male genital anatomy; and pleasurable stimulation to the male genital anatomy. In further embodiments, the aversive stimulation includes at least one of: At least one burst of DC current; and At least one burst of AC current. In another further embodiment, the pleasurable stimulation includes at least one of: An electric current waveform that stimulates sexual arousal; and An electric current waveform that is soothing or relaxing.

In some embodiments, the apparatus further includes at vibrator capable of delivering pleasurable stimulation to the male genital anatomy. In further embodiments, the vibrator employs at least one of: A motor; and An electro-active polymer.

In some embodiments, a stimulus is delivered automatically in response to a prohibited behavior.

In some embodiments, in response to the at least one sensor detecting unwanted activity, stimulation is initiated remotely.

In some embodiments, the apparatus further includes: a remote communication device capable of receiving remote commands to administer stimulation to the male genital anatomy. In further embodiments, the remote communication device receives information of the at least one sensor. In other further embodiments, the remote communication device includes at least one of: A radio transmitter; An optical transmitter; and An inductive transmitter.

Another general aspect of the invention is a male chastity apparatus including: a structural element wearable on male genital anatomy; at least one sensor for detecting unwanted activity relating to the male genital anatomy; and at least two electrodes capable of delivering aversive stimulation to the male genital anatomy.

In some embodiments, the at least two electrodes are also capable of delivering pleasurable stimulation to the male genital anatomy.

In some embodiments, the structural element includes electrodes for electrically preventing or electrically inhibiting removal of the structural element from the male anatomy.

BRIEF DESCRIPTION OF DRAWINGS

The invention will be more fully understood from the following detailed description, in conjunction with the following figures, wherein.

DETAILED DESCRIPTION

Most popular male chastity devices on the market presently rely on a pelvic ring secured behind the scrotum, and a "cage" enclosing the penis attached to this ring, where the testicles and the scrotum are trapped between the pelvic ring and the cage so as to prevent removal of the chastity device. This cage of the device also prevents tactile access to the penis. Examples of this type of chastity device include the CB-2000, CB-3000, CB-6000, and the Curve, each made by AL Enterprises, Inc, Price, Utah.

This type of male chastity device has been successful due to ease of manufacturing. However it has a major drawback. Because the pelvic ring cannot adapt to the changing diameter of the penis in its erect and flaccid states, there is no ideal size for the pelvic ring. When the pelvic ring is tight enough to prevent pulling out the penis even in its flaccid state, it tends to block circulation, especially when the penis becomes erect, or at night. On the other hand when the pelvic ring is large enough for comfort, pulling out (the act of extracting the penis from the cage) is possible when the penis is soft, with lubricant, or in the shower.

By contrast, the male chastity device of the invention ensures that the user will not attempt to pull-out, and that if pull-out is attempted, the wearer of the chastity device will be motivated to re-insert the penis quickly.

The male chastity device of the invention does so by applying an aversive electric stimulus when pull-out is detected, and until the device has been once again secured.

The male chastity device of the invention exploits the fact that the device cannot be removed completely due to either:
- the presence of a scrotal ring 102 such that the ring cannot be removed due to presence of the testicles. The scrotal ring includes two pieces, for example, that are assembled to form a ring that traps the testicles, the ring being difficult for the wearer to remove without help from a tool or a key-holder.
- the presence of a pelvic ring 302 and a housing (also called the "cage") 104 such that the assembly cannot be removed completely because the testicles become trapped in the interstitial space between the ring and the housing Given that the device cannot be removed, the aversive stimulus can be delivered even when the penis is no longer inside the housing 104.

Thus, to prevent pull-out, pull out must first be detected, and then an aversive stimuli motivates reversal of the pull-out. In particular, detection of "pull-out", i.e., the action by which the user tampers with the male chastity device in an effort to remove the penis from an enclosing or surrounding structure, is first accomplished. Then, application of an aversive electrical stimulus upon detection of the pull-out is performed, said stimulus continuing until a push-in is detected.

Pull-Out Detection

Method 1. Force/Pressure Sensing

Figure 3:
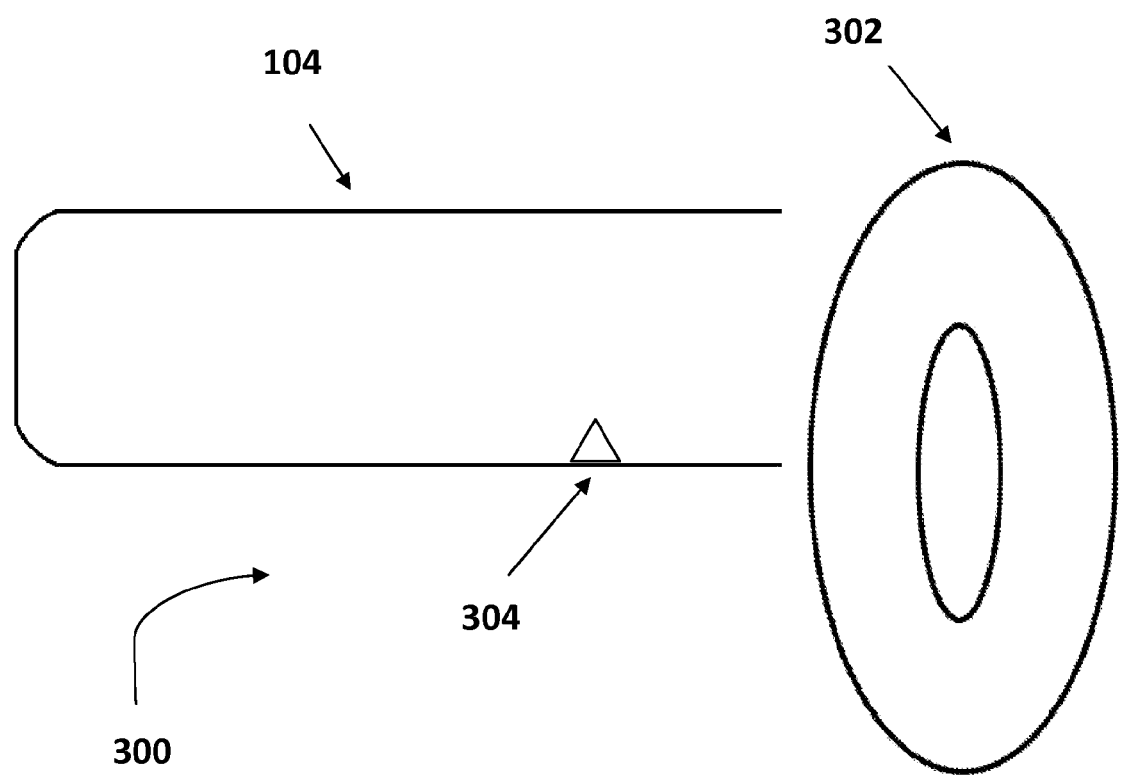
FIGS. 3, 4A, and 4B are schematic diagrams showing a scrotal ring and a penis tube, having various arrangements and combinations of electrodes and/or sensors.

This method detects presence of the penis inside the housing 104 by means of a pressure sensor 304, (such as a push-button switch, a sensor based on liquid or gas displacement, a force sensing resistor, an electromechanical switch that closes an electrical loop, or other mechanical electromechanical, fluidic means). An ideal placement for the pressure sensor is inside the chastity device's cage 104, as shown in FIG. 3. By placing the pressure sensor on the lower half of the housing one can ensure that when the penis is inside the cage, in most cases gravity will produce sufficient downward force to create a reading from the pressure sensor.

Force Sensing Resistor (FSR): A force sensing resistor is a thin (<1 mm), flexible sensor which varies its resistance as pressure is applied to it. It enables simple external circuitry to detect the amount of pressure being applied. A FSR or similar sensor can be used to detect the amount of pressure on a structure enclosing the penis. When pressure falls to zero, the device can assume that the penis has been removed from the structure 104 (pull out). However detecting a "push in" in this way is more problematic because pressure could be exerted by another object (such as a finger). Despite the simplicity of pressure based sensing, FSRs are still quite expensive; additionally the threshold for detection is such that it may not always be reached by the pressure exerted by a flaccid penis. Therefore this approach, though amenable to improvements, yields crude results if it is not complemented by additional strategies for detection, such as those listed below.

Conductive rubber is an alternative to FSRs. Like FSRs, a conductive rubber part can be used to obtain a quantitative measurement of the pressure being exerted on a part. However, the manufacturing costs for a part of this kind are a lot cheaper than FSRs (cents per piece as opposed to tens of dollars). The use of conductive rubber also offers easy waterproofing compared to FSRs, because FSRs may be damaged by water. The same rubber component used to measure pressure will also form a water tight seal between structural parts, protecting an underlying circuit board. In an example embodiment (not shown), the single sensor 304 is embodied as two distinct contact points (304A and 304B) separated by some distance. The conductive rubber part (possibly shaped like a curved sausage) connects these two contact points and protrudes inward from the penis housing. When the penis is present, pressure on the conductive rubber part will create a conductive path between 304A and 304B closing a circuit. The resistance between 304A and 304B can be measured, and it yields a measurement of the force experienced by the conductive rubber. The stronger the pressure, the better the conductive rubber will adhere to the underlying circuit board contact points. Good adhesion results in lower resistance. The conductive rubber method suffers from one of the limitations of the FSR: under normal circumstances it is not always possible to provide it with enough pressure to distinguish between a pull out and a flaccid penis. For these reasons, force resistors are better suited to detect unwanted behaviors such as erections, which produce substantial pressure, and are not an ideal presence sensor.

Method 2. Optical Method (Infrared/Near Infrared/Heat Sensor)

The sensor 304 can include a photodiode. The photodiode will sense the temperature or optical emissions of neighboring anatomy, within or near the infrared spectrum. The sensor's output can be used to determine whether the penis is inserted into the housing 104.

Temperature will be quite high (average body temperature or above) when the penis is present, and much lower when it is not. Push-in can be detected more reliably than with a force sensing method, because substituting a different object (such as a finger) will not produce the same heat signature. Additionally the IR sensor is not affected by the same drawbacks of force sensors, because it has no "minimum" activation energy. An IR sensor can detect a flaccid penis exerting no pressure whatsoever onto its surrounding structural parts.

As a further improvement, rather than just detecting a heat signature, the photodiode could be sensing reflected and refracted light emitted by the device itself in useful regions of the spectrum. In this case both a light emitting diode (LED) and a photodiode would be placed inside the housing. Near infrared spectroscopy (NIRS) is well known and it has been applied to urology ("Urological applications of near infrared spectroscopy" by Stothers et al.)—in particular oxygen transporting hemoglobin has a different signature in the infrared spectrum from poorly oxygenated hemoglobin. This difference is already being used in urology to diagnose erectile dysfunction. Under normal circumstances, when blood is flowing to the penis (such as in case of an erection) that blood is oxygen rich and produces a different IR signature. This fact can be used to detect erections by probing the IR spectrum according to known means. However, due to existing intellectual property, design considerations, and processing requirements, erection is best sensed by mechanical means, and infrared is best used as a presence sensor.

Another consideration is that when a "shine+detect" method such as the one above is used, one no longer needs to be limited to using the infrared part of the spectrum. Visible light can be used in the same way, by using a regular light emitting diode and a detector of optical energy in the same wavelength. Visible light, just like IR is reflected and refracted by surrounding tissue. Furthermore the rate of reflection and refraction is different for different wavelengths. Therefore the most sophisticated embodiment of the optical detection system actually involves a comparison of the reflection/refraction characteristics sampled at different wavelengths. In concrete terms, this is embodied as one visible light LED, one visible light photodiode, one infrared LED and one infrared photodiode. This level of sophistication however results in added component cost and a greater number of possible points of failure. The complexity just described can easily be avoided, by using only one wavelength, but relying on different sensor types (pressure and optical, for instance). Best results are given by analyzing data supplied by different kinds of sensors, rather than trying to achieve 100% accuracy in interpreting the output of one type of sensor, or trying to improve the sensor such as in the multiple wavelength approach described.

The ideal position of an optical sensor is about half way through the cage. This position guarantees that the presence of penises of different lengths will be detected correctly, but also that the penis will need to be inserted sufficiently deeply into the cage before the sensor's reading changes. Multiple IR photodiodes can be used across the length of the penis housing increasing the data available for analysis. In particular, multiple IR photodiodes allow the device to sense when the penis is completely inserted, as opposed to being partially inserted—the variance in penis length across wearers can thus be accommodated, through an initial "Setup" phase which instructs the device to use one particular sensor as presence detector. For instance, a wearer with above average penis length may choose to use the sensor that is farthest away from the base of the penis as a presence sensor. Wearers with shorter penises may use sensors that are closer to the base of the penis. Optoelectronic components such as photodiodes are very inexpensive, so this method offers many advantages. Multiple sensors longitudinally placed along the length of the penis housing can even produce a clear direction and speed reading with respect to the pullout being attempted, because the position of the penis at three different times can be obtained; however, this level of complexity is not needed for reliable detection when multiple sensor types are employed.

Figure 4A:
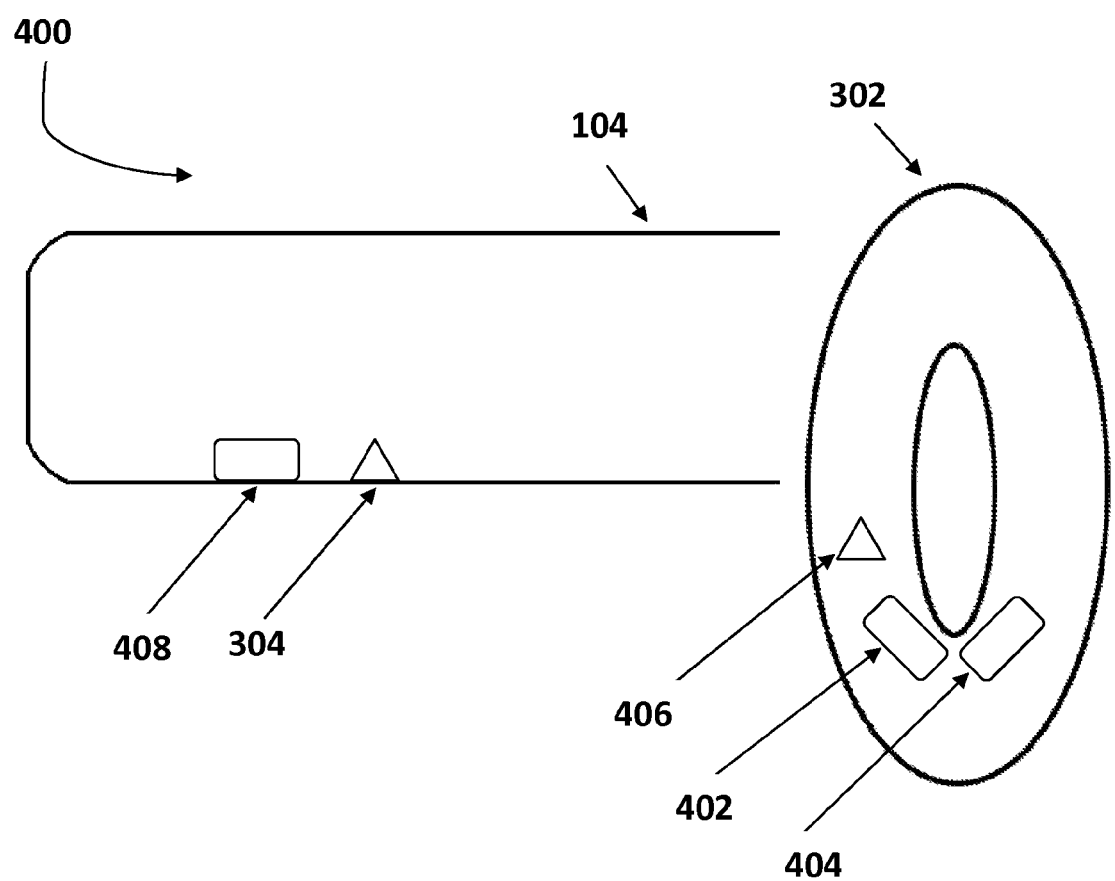

Method 3. Electrical Resistance Estimation (FIG. 4A)

Figure 4B:
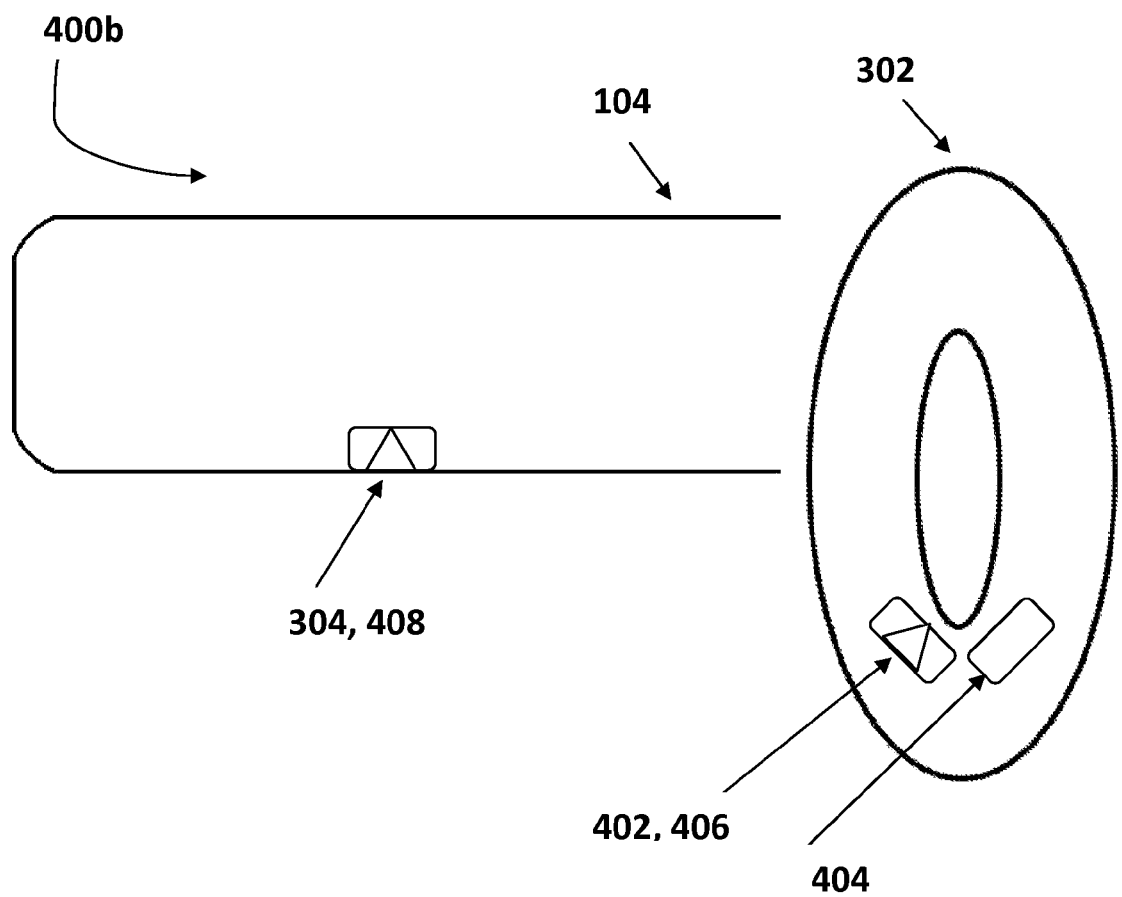

In this method the sensor 304 is an electrical contact, and a supplemental electrical contact (406) is also present. Electrical resistance between them is measured electronically. The two electrodes are electrically connected through the penis when the penis is inside the cage 104, but they are not electrically connected when the penis is not inside the cage 104. Because electrical resistance across, for instance, a finger, is much higher than between two neighboring points on a penis, this method can most reliably detect pull-outs and push-ins. Resistance can be estimated electronically by well known means. FIG. 4B shows a variation of the method described, where one of the electrodes 304, 408 and 402,406 used for delivering an aversive stimulus doubles as a contact point for resistance estimation to reduce the number of needed parts (an electrode is, after all, a simple electrical contact point, just like the sensors in this method).

The methods and sensor types listed above may be combined for extra reliability of detection. For instance, in the already described case of infrared presence detection and conductive rubber erection detection. Also, the most effective method (electrical estimation) can be combined with other methods when it is desirable to reduce the amount of current flowing through the body. In this case the more reliable resistance estimation method can be used to detect a first insertion of the penis (when the previous presence reading is negative); afterwards infrared sensing can be used to detect pull-outs. Current only flows once whenever the penis is inserted. In this way current flowing through the body can be minimized without penalizing the accuracy of the detection. In synthesis, having explored a large variety of mechanisms, the best embodiment is represented by a mixture of electrical, optical, and force sensors. This allows accuracy, easy and inexpensive manufacturing, and minimization of electrical current used for detection.

Sensed data may be used in this invention
 a. For reporting purposes (such as reporting the events to another person at a later point in time)
 b. To drive the device's automatic deterrent measures such as the electrical stimulus When data is to be reported, an issue arises concerning the transmission of said data for reporting. Unless means for reporting are embedded into the device data will need to be moved out of the device and into another electronic device (such as a personal computer which can eventually post the data to a network).

Due to the size constraints of wearable devices and battery capacity restrictions, LCD screens and on-board LEDs are not a good way of reporting detected states. Instead, said states can be transmitted to an outside system by:
 a. A data port such as a USB port
 b. A wireless connection A USB port creates the problems of waterproofing and tamper proofing the connector. Because the chastity device is normally used over a span of several days at least, the device must allow the wearer to bathe and shower. A rubber plug will easily solve the water-proofing problem but not the tamper proofing problem.

Waterproofing and Tamper Proofing the Data Connector

One way to solve the issues described above involves creating a complex plug for the data connector. The plug is made of a hard material such as plastic, and it has a rubber ring along its perimeter so that it will create a water proof seal with the main body of the device. Two custom head screws are used for securing the plug when the device is in data acquisition mode. When data is to be transmitted, and a USB link to be established, the chastity keyholder or device controller opens the plug with a special screw driver.

Unfortunately, the method above involves manufacturing complexities. Furthermore the controller must be present when the data link is established. So tamper-proofing is incompatible with automatic remote reporting. It is in other words not possible for the controller to receive periodic "digests" through a network and monitor the wearer's activity without regular maintenance of the data link.

A more advanced solution to this problem involves using radio transmitters. The chastity device can carry an on-board radio transmitter, which can establish a data link with a separate USB peripheral. The USB peripheral will relay data to a PC. Radio transmission requires expensive certifications and components, but it does not involve maintenance and it can help achieve easy water-proofing. Additionally it opens up further control possibilities, such as activating the aversive stimulus through the use of a remote control. With wireless transmitters the range is easily tens of meters, and reporting can occur at regular intervals without the intervention of the wearer or the controller.

A third inexpensive solution for data link consists of a wireless connection that does not rely on Radio Frequency. In one embodiment, an infrared LED and an infrared optocoupler are housed within the chastity device and point outwards through the device's housing. The chastity device's main body is transparent to infrared light. A data link can be established with a personal computer through a separate USB peripheral which features a similar pair of IR transmitters/receivers. Essentially a low data rate modem pair carries data bidirectionally, encoded in infrared light pulses. A mono-directional data transfer can be created even more simply with the chastity device having only the IR LED and the USB peripheral only housing the optocoupler.

Finally another possible solution is the use of inductive coupling. In this method an inductive metallic loop is energized by the chastity device, producing a magnetic field. Energy is transmitted through the field and converted back to electricity by a similar loop held very close to the device, and connected (possibly through a cable) to a USB peripheral. These inductive loops function just like the LEDs in the example above, except that the same component both transmits and receives data. Inductive coupling is well documented. This method is technically interesting and uncommon, however the LED method achieves the same result with much lower complexity and is preferred.

Therefore the best data link methods for a device which seeks to report recorded states to the outside are:
 1. Wireless transceivers (where remote control activation is desirable)—this yields maximum flexibility with long range, though there are high regulatory burdens and component/development costs
 2. IR LED/IR optocoupler bidirectional data link (cheapest and simplest method available, gets the job done well if long range is not required)

A periodic data link can be made tamper-proof by using bidirectional data transfer in the following fashion. The chastity device requires an acknowledgement of transmitted data every N hours/days. When the acknowledgement is not received the chastity device will deliver aversive stimuli with increasing frequency. When the data link has finally been established and data has been exchanged, the time counter is reset and the device will not require another data transfer for another N hours/days.

Application of Aversive Stimulus

Aversive electric stimuli are commonly used for behavior control and training of animals. A common application consists in remote control dog training collars. Here some improvements are introduced which enable the same type of training to be applied to human subjects, particularly in the context of miniaturized personal wearable devices.
 1. A type of aversive electric pulse (waveform) 200 which is more humane and easily tolerated than the AC current used in most estim products (FIG. 2)
 2. A method for producing this current pulse using a small lithium ion battery, which results in considerable miniaturization and wearability compared with common estim products utilizing bulky 9V alkaline batteries

3.

Electric Pulse

Figure 1:
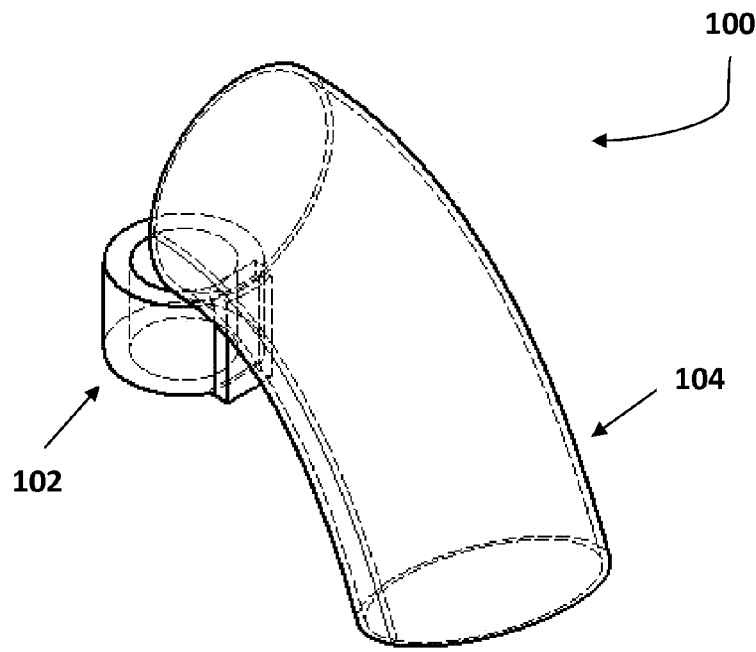
FIG. 1 is a three-dimensional transparent view of a scrotal ring attached to a penis tube for confining a penis of a male genital anatomy.
Figure 2:
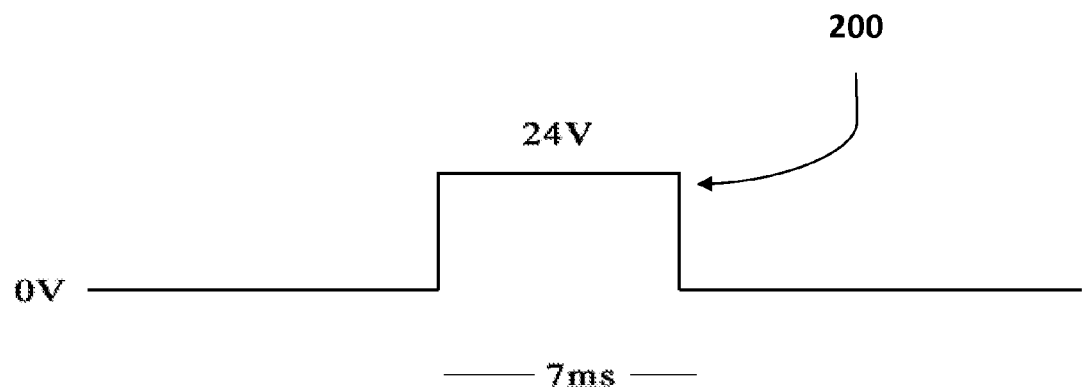
FIG. 2 is a plot of voltage versus time showing a signal waveform.

The current pulse 200 shown in FIG. 2 consists in a short burst of current between 10 and 40V. Though the voltage is constant, the perceived intensity of the stimulus can be modulated by changing the delivery time, from less than 1 ms to 15 or more ms, and by changing the number of pulse repetitions in one stimulus.

At the lowest empirically determined optimal setting, the pulse is DC current and its duration is 7 ms. At medium setting the duration is 15 ms. At the highest setting two 7 ms pulses (2 cycles) are repeated in short succession with an interval (no current) of 7 ms. Additional cycles increase the perceived intensity of the pulse; increasing cycles effectively turns the DC pulse into an AC one. For most practical purposes a single DC pulse delivers the humane, easily tolerated aversive sensation. The lowest setting pulse waveform 200 is shown as an example in FIG. 2.

Delivery Circuit

Figure 5:
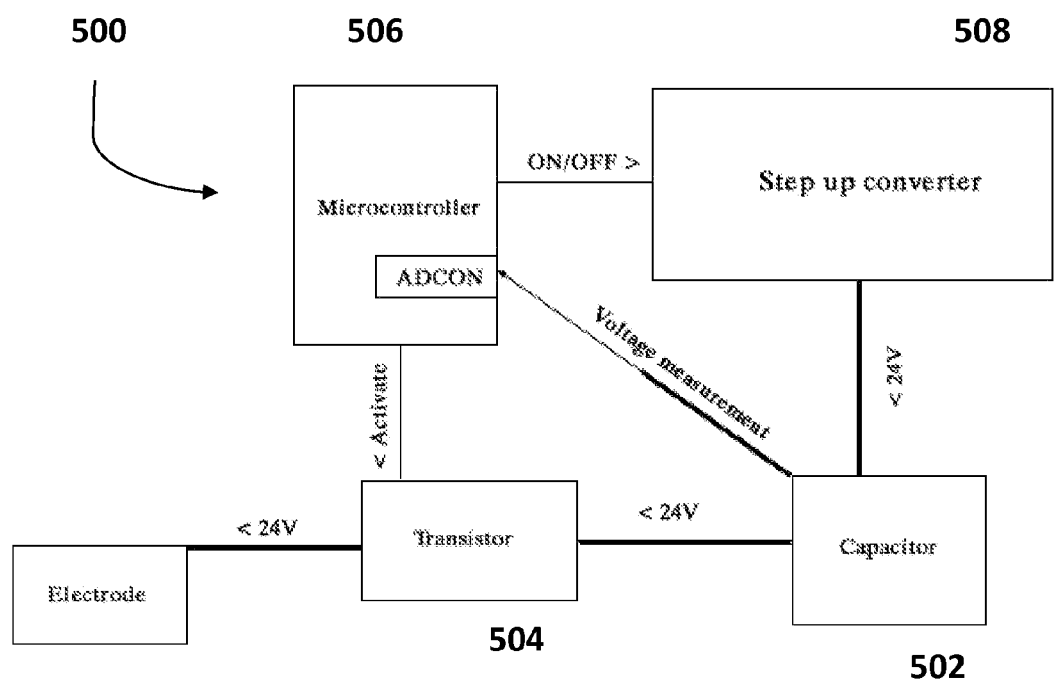
FIG. 5 is a circuit diagram showing how a microcontroller of the chastity device controls at least one electrode of the chastity device to deliver the pulse shown in FIG. 2.

With reference to FIG. 5, the delivery circuit 500 consists of a step up converter integrated circuit 508, a capacitor 502, a transistor 504 and a microcontroller 506 with an ADC module (Analog to digital converter). The input voltage and current for the circuit can easily be supplied by a lithium ion battery. Spiral type high drain lithium thionyl chloride cells have good power density and are capable of producing high instantaneous currents needed for voltage up-conversion. However they are not rechargeable. Lithium polymer packs have good power density, can produce high currents and are rechargeable, thus, they represent the best choice.

Figure 6:
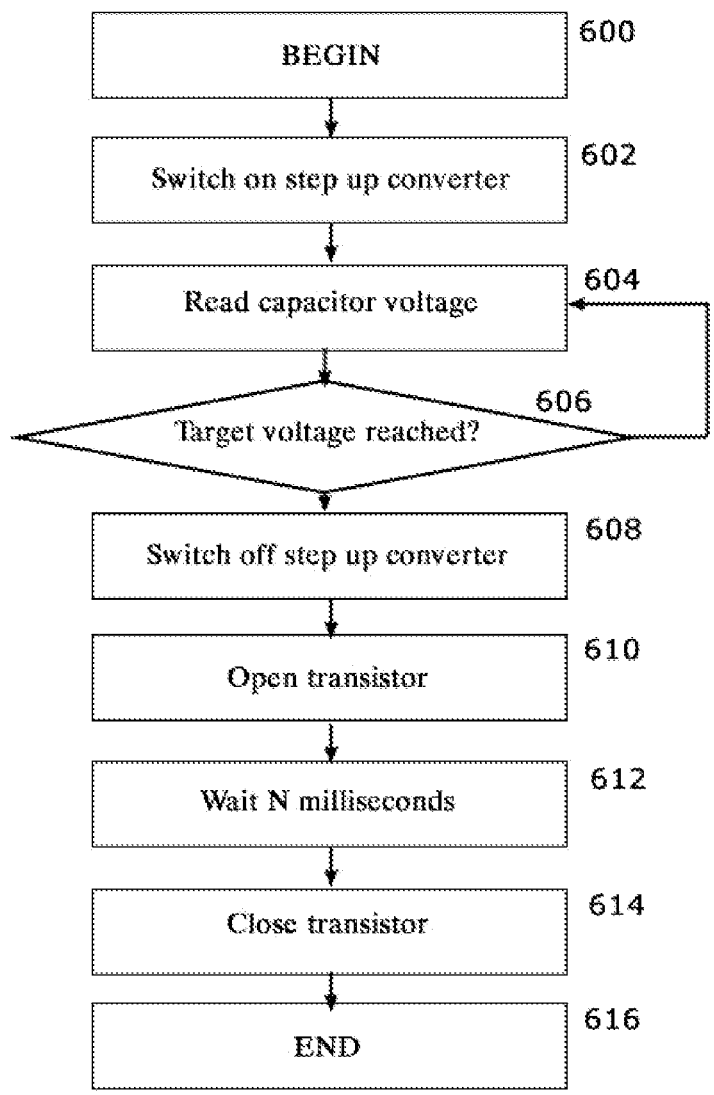
FIG. 6 is a flow chart showing steps executed by the circuit shown in FIG. 5.

With reference also to FIG. 6, when the microcontroller activates the step up conversion by taking the step up converter out of standby mode (step 602), the 3.6V input current is converted into 24V by the converter IC, and the capacitor 502 begins to charge. At this point the transistor 504 is inactive, so no current can flow to the electrodes. The microcontroller's ADC module senses the voltage through a voltage divider (two resistors in series) which enables it to sense voltage above the microcontroller's own input voltage (step 604). When the target pulse voltage has been detected by the microcontroller, it places the step up converter 500 back into stand-by mode (step 608), then it opens the transistor 504 (step 610) for a number of milliseconds (step 612). When the pulse has been delivered the transistor is switched off (step 614).

The diagram in FIG. 5 illustrates the interconnections between the components. Thin lines represent logic signals, and thick lines represent high voltage pulse current.

FIG. 6 shows a flow chart outlining the process of pulse delivery.

Tamper Proofing Current Delivery

Tamper-proofing the device in such a way that the wearer cannot interfere with the delivery of the aversive electrical stimulus requires using multiple electrode pairs and multiple sensor pairs. These are not shown in the figures for sake of simplicity.

Multiple electrode pairs: essentially instead of one positive and one negative electrode, the device can use a multitude of positive electrodes (electrically connected) and a multitude of negative electrodes (also electrically connected). These can be distributed radially around the structural rings shown in the figures, or placed at strategic locations.

Multiple sensor pairs: these are electrically separate pairs of contact points placed near electrode pairs.

Mechanism: the wearer may attempt to prevent the delivery of the aversive stimulus by placing some material (a finger, or a piece of paper) between the contact points and the skin. When multiple pairs of sensors and electrodes are used, the device is able to sense this sort of tampering and trigger aversive stimuli from the electrodes still making contact with the anatomy. This discourages such attempts and prevents tampering.

Deterring Unwanted Behavior by Eliminating Pleasurable Stimuli

In some cases unwanted behavior can be deterred by delaying or cancelling an on-going cycle of pleasurable stimuli in response to the detection of said behavior. Pleasurable stimuli can include sexually arousing types of electric stimulation, vibration, and/or movement generated by an on-board motor, and/or movement and contraction/expansion of advanced materials such as electro-polymers which change shape or size when a current is applied. Sexually arousing types of electrical stimulation are known and utilized in many e-stim devices such as those made by Erostek and PES.

Anti-Pull Out Embodiments

Case 1. Simplest Case (FIG. 4A)

The device has 2 electrodes (402 and 404) which may be mounted on or below the scrotum, and two sensor terminals 304 and 406. The sensor terminals (contacts) will be in contact with the penis so that the resistance between the two can be used to detect the presence of the penis.

The device can deliver an electrical pulse through electrodes 402 and 404 and also measure the electrical resistance between either 304 and 406

If the wearer tries to slide his penis through the device in such a way as to remove it from the cage (something that is often possible with common chastity device designs) at some point the penis will cease making contact with the sensor 304. At that point, the resistance between 406 and 304 will change, and the device will know that the wearer is attempting a pull out. Then, the device will trigger an electrical waveform which will be delivered between electrodes 402 and 404, until the wearer reestablishes contact between the penis and the sensor, thus ensuring that the device is once again worn snugly.

FIG. 4B illustrates a simple adaptation of the same embodiment in which one of the electrodes also functions as a sensor terminal. Essentially the metallic contact needed to measure resistance and to deliver a current pulse is identical, hence this embodiment can be used to reduce complexity.

Case 2. Trans-Penile Current Delivery

This method is intended for devices which can also administer an electric stimulus for other reasons than a pull-out (ex. To deter an erection, or upon reception of a wireless signal)

This method enables the device to administer two types of electrical stimuli.

In this device, either the sensor 304 has a double function, and is both an electrode for current delivery and a sensor, or there is a third electrode in close proximity of sensor 304. In FIG. 4A this optional extra electrode is labeled as 408.

Due to the presence of both an electrode and a sensor within the housing (or the double use of the contact point 304 as electrode and sensor), the device can not only deliver an electrical pulse through the penis, but also measure the electrical resistance at the two ends (between 406 and 304)

The electric pulse that can be delivered between the scrotum and the penis (contact points 402 and 408 or 404 and 408) yields a much less electrical feeling and a more bearable aversive pulse 200 by allowing the current to have a small or null AC component. By contrast, the electric pulse that can be delivered between 402 and 404 requires a strong AC component in order for the pulse to feel like something.

When a wirelessly transmitted signal is received from an external transmitter or controlling apparatus, or when an unwanted behavior other than pull-out has been detected and the penis is still inside the housing, the wearer will receive a DC pulse between electrodes 402 and 408 (or 404 and 408). This pulse requires the chastity device to fit snugly around the wearer's penis However, if the wearer tries to slide his penis through the device in such a way as to remove it from the cage (something that is often possible with common chastity device design) at some point the penis will cease making contact with electrode/sensor 304. At that point, the resistance between points 406 and 304 will change, and the device will know that the wearer is attempting a pull out. At that time, the device will trigger a more aversive AC (alternating current) shock which will be delivered between electrodes 402 and 404, both situated on the scrotum or at another location that is not affected by the wearer's attempts to pull out, until the wearer reestablishes contact between the penis and the housing electrode 304, thus ensuring that the device is once again worn properly.

Cageless Chastity Device

The cageless chastity device is an electronic device mounted on a male's genitals. The difference between this type of structural assembly and other commonly used chastity devices is that the cageless device does not need to enclose the penis with a housing or cage 104. Sexual intercourse and masturbation are prevented by detecting erections and/or movements/vibrations electronically (mainly through motion sensing) and delivering an aversive electric pulse to the genitalia to discourage these types of actions. An example of embodiment is a ring type device that encloses all necessary electronic components. The ring can be secured around the penis behind the scrotum (pelvic ring 302) or around the scrotum (scrotal ring 102, more secure). Vibrations typical of manual stimulation and intercourse can be reported by an accelerometer and analyzed by a microcontroller, as described herein below.

Such a device may also include a way of detecting an erection through one or more of the sensors described above (force, infrared etc), mounted within the ring. Whether the user seeks to prevent erections altogether, or allow erections but discourage having an orgasm, will affect which sensing mechanism the user decides to enable.

Most practical problems related to common chastity devices can thus be completely avoided by this cageless embodiment. Such problems include devices that can split at their seams and pinch delicate tissue, the ability to "pull out" when the ordinary (cage based) chastity device is not tight enough, blocking of circulation when the same device is too tight, general discomfort, the device showing through clothing and more.

Figure 7A:
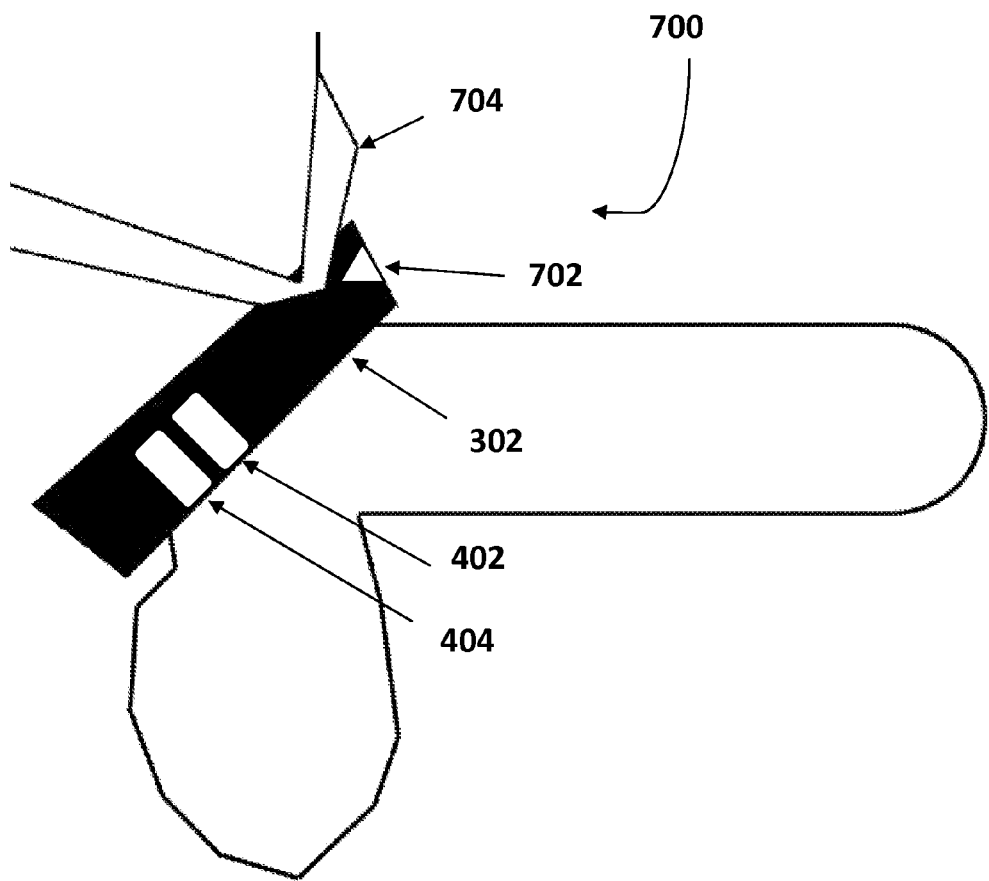
FIG. 7A is a schematic diagram of male genital anatomy showing a pelvic ring having at least one electrode and at least one sensor, also including a waist strap.
Figure 7B:
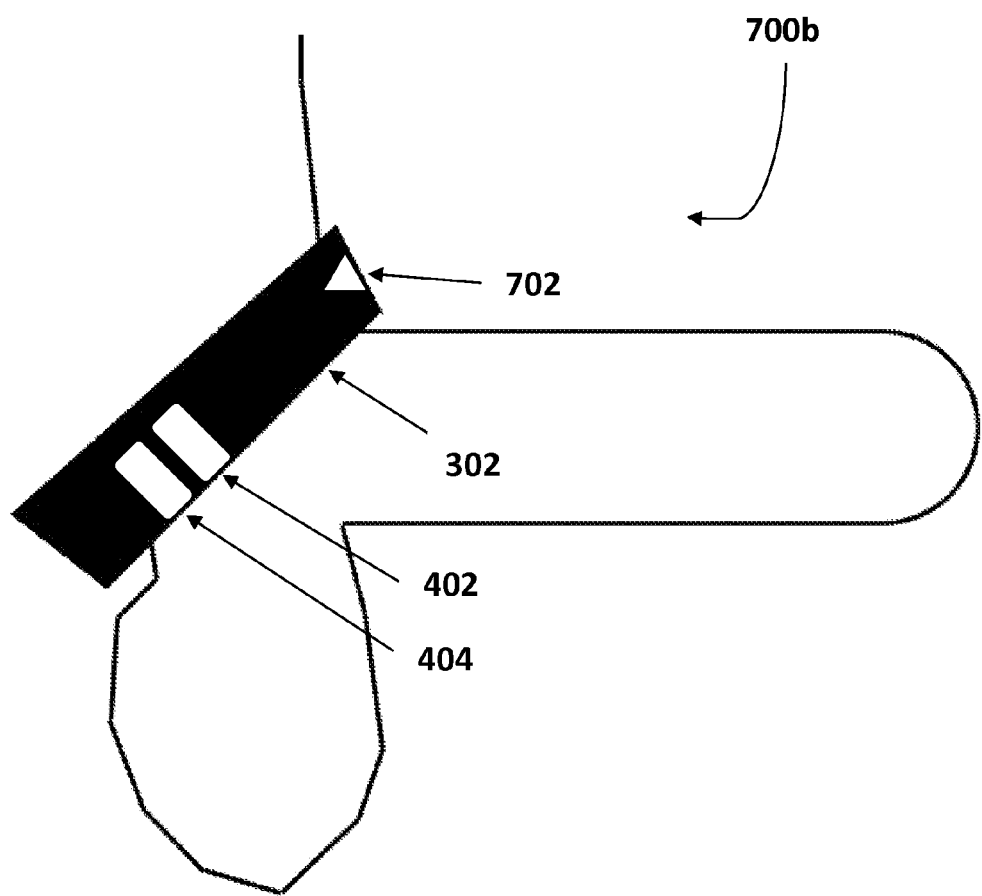
FIG. 7B is a schematic diagram of male genital anatomy showing a pelvic ring having at least one electrode and at least one sensor.

Sample Embodiment for the Cageless Male Chastity Device:

In the simplest embodiment (FIG. 7A), the circuitry is contained in a plastic ring 302, and the ring is held in place by a strap 704.

The electronics include an accelerometer integrated circuit 702 which converts acceleration data into digital signals, and a microcontroller that interprets these signals. The microcontroller applies some algorithms or pattern recognition in order to discern ordinary movements, such as walking, and movements that are possibly intended to stimulate the wearer (masturbation, vibrators, intercourse). The tri-axial accelerometer data (x, y, z acceleration) is recorded in a data buffer (microcontroller EEPROM). Every N samples an algorithm is applied to recognize a specific wearer activity and possibly administer an electric pulse to deter it.

The algorithm includes a naïve bayes classifier using mean, standard deviation and correlation as features. A total of 9 features are extracted at each calculation interval, from the previous 256 collected samples. These features are:

Mean X, Mean Y, Mean Z, Std dev X, Std dev Y, Std dev Z, Correlation X-Y, Correlation X-Z, Correlation Y-Z The values are compared against data obtained in a training phase, in a naïve Bayes classification.

A description of this method can be found on "Activity Recognition from Accelerometer Data" by Nishkam Ravi et al.

Training Phase:

This includes exposing the learning algorithm to different patterns of activity, both those which should be allowed and those which should be deterred. The user specifies which activities are considered "allowed" and which aren't, using an interface residing on a personal computer, to which the cageless chastity device connects wirelessly.

The algorithm discretizes the data into "buckets" of equal size, and stores the results which are used for later real-time recognition.

Enhanced Embodiments

It will be possible to enhance the accuracy of the algorithm by:

Adding additional accelerometers and/or gyroscopes and feeding their data into the algorithm in a parallel fashion (for instance, with 2 accelerometers there would be 18 features fed into the bayes classifier instead of 9)

Adding features that encode periodicity, such as energy (sum of the squared discrete FFT component magnitudes of the x, y, z signals divided by sample size). In a one accelerometer case, this would increase the number of features to 12

Using enhanced discretization methods (instead of equal width buckets, a number of alternatives exist such as Equal Frequency Discretization, Fuzzy discretization, Entropy Minimization Discretization, Iterative Discretization, Proportional k-interval Discretization, Lazy Discretization, Non-disjoint discretization, Weighted Proportional k-Interval Discretization,). These are explored in "A Comparative Study of Discretization Methods for Naive-Bayes Classifiers" by Ying Yang & Geoffrey I. Webb (In Proceedings of PKAW 2002, The 2002 Pacific Rim Knowledge Acquisition Workshop, Tokyo, Japan, pp. 159-173.)

The exact placement of the accelerometer will determine the pertinence of the recorded acceleration patterns to the stimuli that need to be recognized, and hence the accuracy of detection. There are a few issues to be considered when placing the accelerometer:

Distance from the stimulation point (usually the penis shaft and in particular the frenum). For example, mounting the accelerometer around the glans will yield more accurate pattern recognition than mounting it at the base of the penis Attenuation of vibration due to anatomy. Example: though the abdomen is physically close to the penis shaft, it does not vibrate much, and it therefore constitutes a poor placement point Ability to manually interfere with the accelerometer's functioning. Example: mounting the accelerometer on the scrotum makes the device susceptible to tampering: the wearer could hold the scrotum still while stimulating himself, and the accelerometer would detect a much reduced vibration intensity.

Limitations to the physical details of the enclosure (due to material properties, anatomy, wearability constraints, and other product constraints).

Cageless Embodiments

The embodiments which enable the most favorable and secure accelerometer placements follow.

Figure 8:
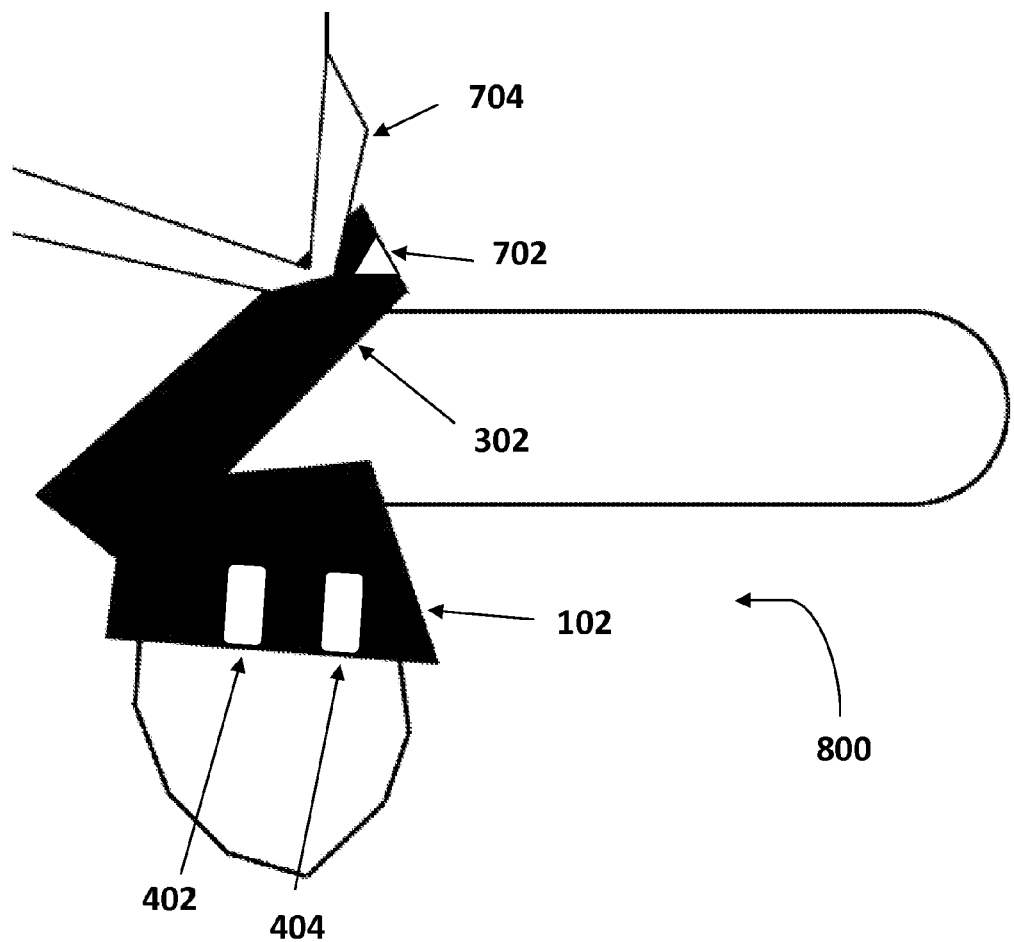
FIG. 8 is a diagram of male genital anatomy showing a waist strap, a pelvic ring having at least one sensor, and a scrotal ring having at least one electrode.
Figure 9:
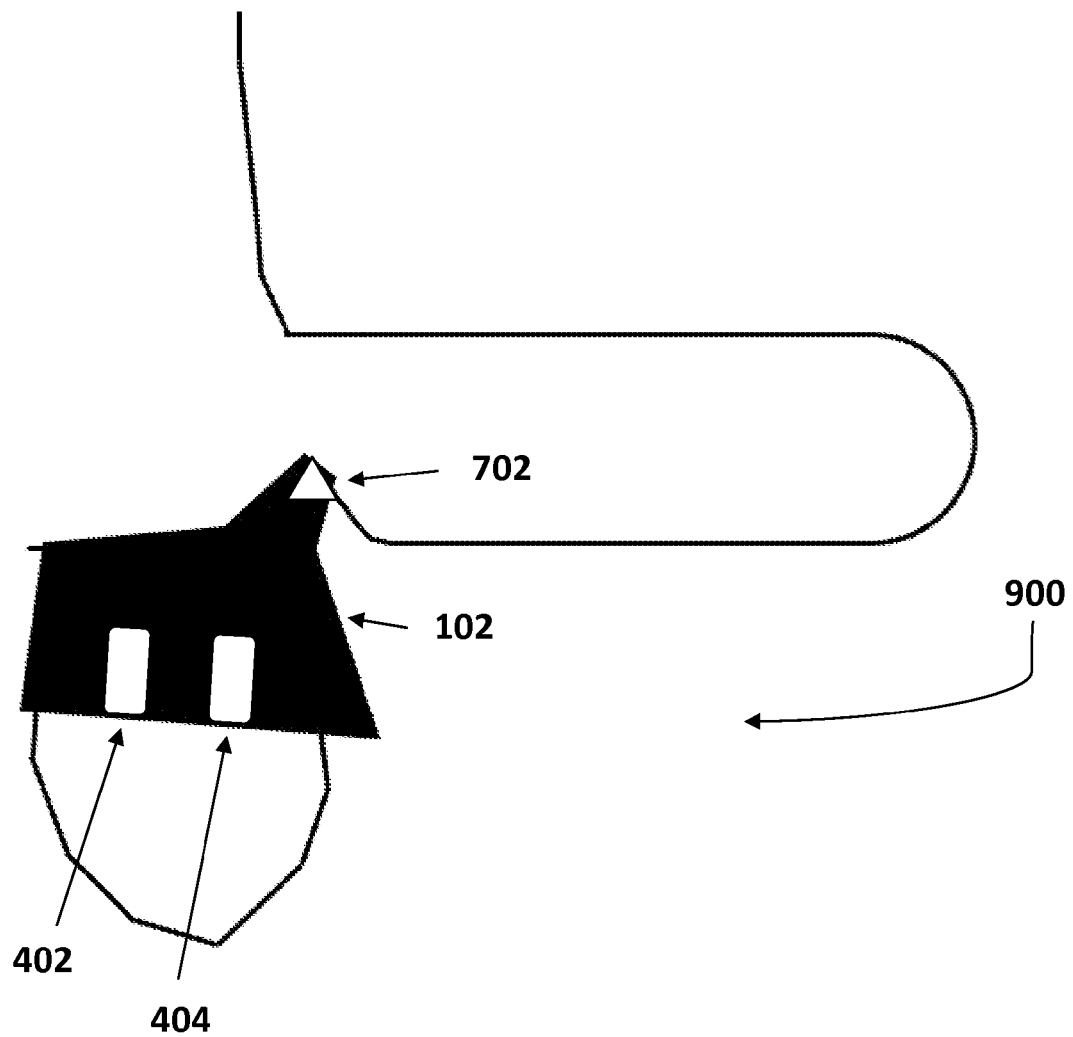
FIG. 9 is a diagram of male genital anatomy showing a scrotal ring having at least one electrode and at least one sensor.
Figure 10:
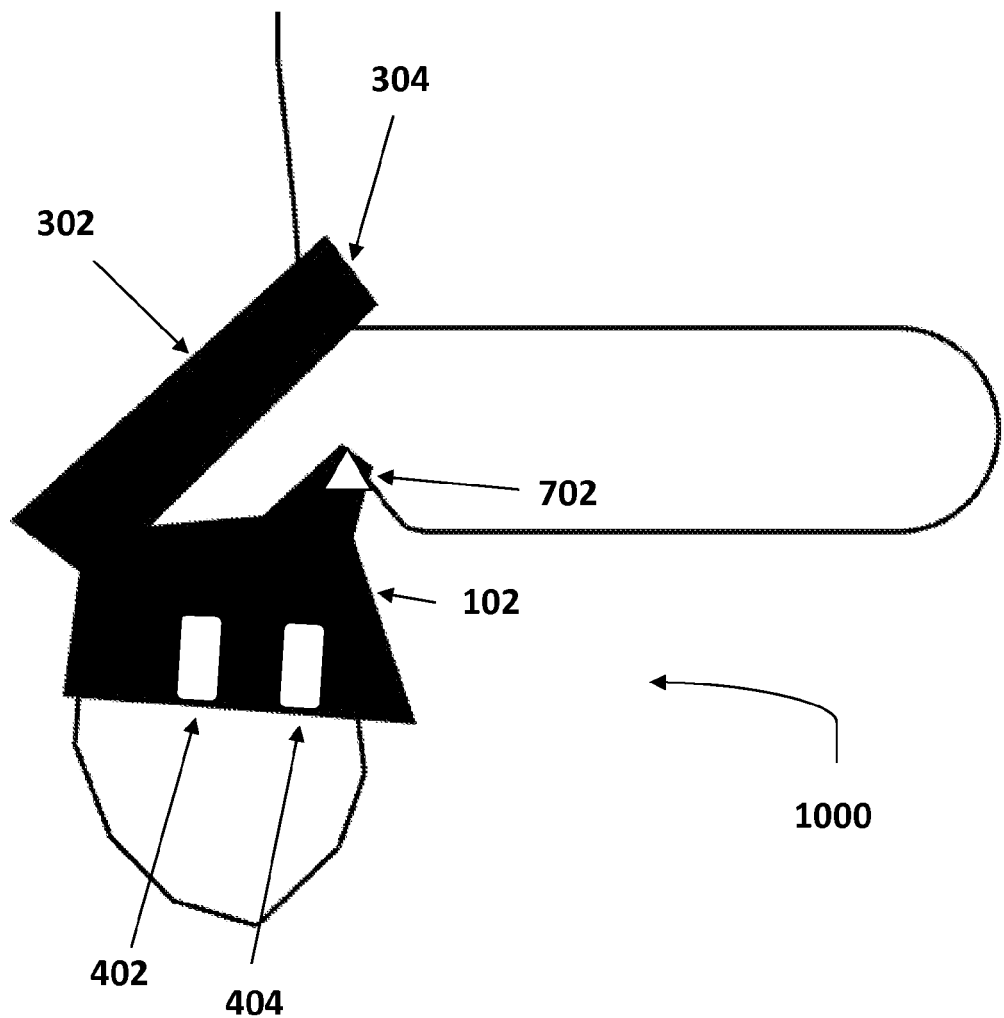
FIG. 10 is a diagram of male genital anatomy showing a pelvic ring having at least one sensor, and a scrotal ring having at least one sensor and at least one electrode.
Figure 11:
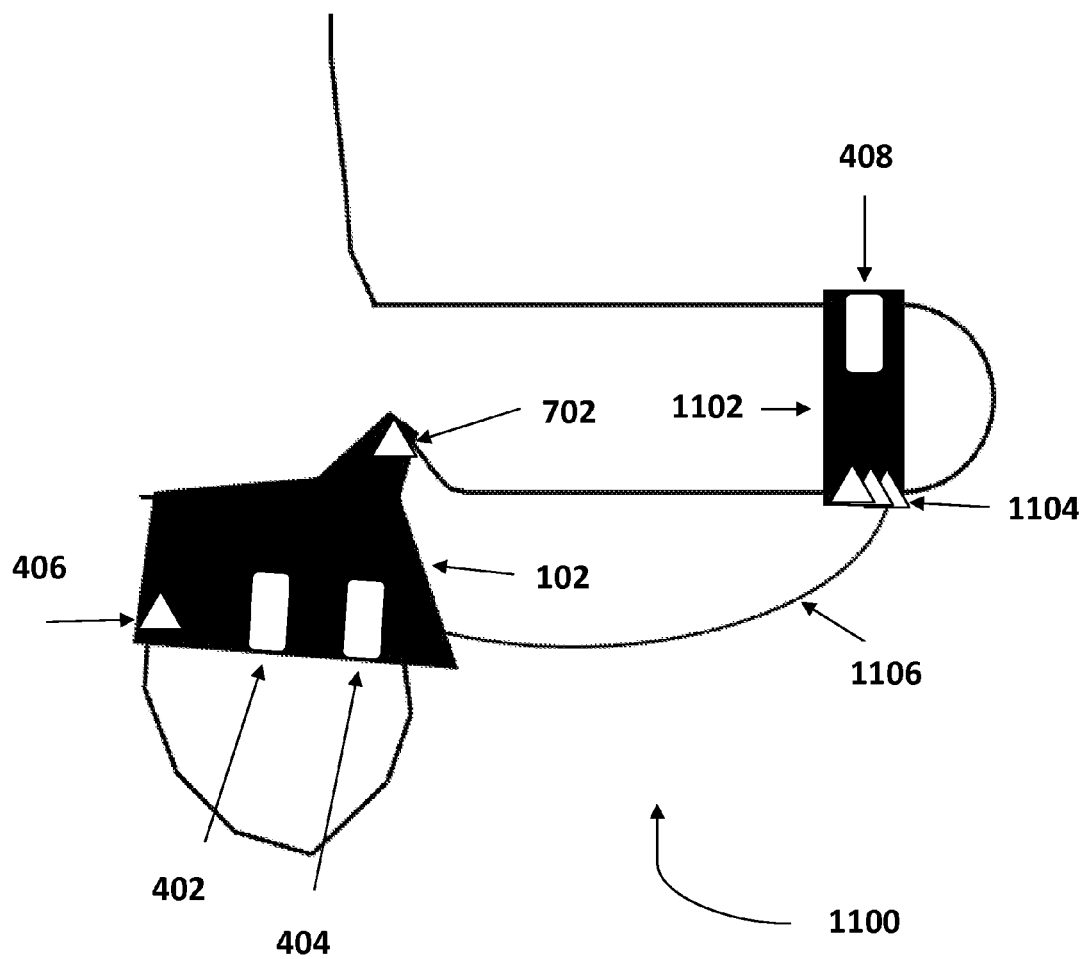
FIG. 11 is a diagram of male genital anatomy showing a glans ring having at least one sensor and at least one electrode, and a scrotal ring having at least one sensor and at least one electrode.

1. Pelvic ring 302 type cageless chastity device, top accelerometer 702 placement, waist strap 704. Pelvic ring can contain erection sensor (force sensing resistor or other type) (FIG. 7A)
2. Pelvic ring 302 type cageless chastity device, top accelerometer 702 placement, scrotum ring 102 containing electronics, waist strap 704. Pelvic ring can contain erection sensor (force sensing resistor or other type) (FIG. 8)
3. Scrotal ring 102 type cageless chastity device, scrotal accelerometer 702 placement, scrotal ring also contains electronics. Note that accelerometer is placed on a protruberance with the intent of ensuring maximal contact between the penis shaft and the scrotal ring, and to transmit vibration (FIG. 9)
4. Scrotal ring 102+pelvic ring 302 type cageless chastity device, scrotal accelerometer 702 placement, scrotum ring also contains electronics. Note that accelerometer 702 is placed on a protruberance with the intent of ensuring maximal contact between the penis shaft and the scrotal ring, and to transmit vibration. Pelvic ring can contain erection sensor 304 (force sensing resistor or other type). Pelvic ring can contain pull-out sensor (force sensing resistor, infrared sensor or other type). There is no waist strap in this design; when the penis is in its soft state, it is possible for the user to try to remove the pelvic ring ("pull-out") by sliding the penis through it. However, this action will be detected, and electric pulses will be delivered though electrodes 402 and 404 placed on the scrotal ring 102 until the penis is re-inserted into the pelvic ring 302. Detection of pull-out can happen by measuring the output of a sensor 304. In case of a force sensing resistor, this sensor can also be used to detect erections. When the penis is erect the FSR will be compressed and its resistance will drop. When the penis is in its normal state the FSR will signal an average resistance. When pull-put occurs, the FSR will have maximum resistance (no compression). In the case of an infrared sensor, pull-out is sensed when the reading drops. Or, detection of pull-put can happen by electrical means (calculation of resistance between two electrodes 402 and 304, or 404 and 304). Or, accelerometer 702 reading combined with the above two data can be used (to slide the penis out of the pelvic ring 302, it is likely the wearer will need to tilt the assembly forward and this can be detected through the accelerometer) (FIG. 10)
5. The most advanced embodiment (FIG. 11) includes a glans ring 1102 which is placed around the glans of the wearer and connected to the main body of the device through a cable 1106. The glans ring 1102 is partly or entirely made of stretchable material (such as rubber) which guarantees it will fit snugly in place unless it is removed. The glans ring hosts the third electrode 408 and a second sensor assembly 1104. The sensor assembly 1104 includes an accelerometer, an infrared diode and optocoupler, and an electrical contact used as a sensor. In this embodiment the wearer is responsible for maintaining the glans ring properly positioned. The device detects when the glans ring 1102 is removed, or when the cable 1106 is cut. The glans ring 1102 provides an optimal placement for an additional accelerometer. In this embodiment the output of two accelerometers (702 and 1104) is compared. By comparing the output of two accelerometers it is possible to analyze the movement of the penis with respect to its base. This makes the task of detecting any sexually arousing activity a lot easier, due to the higher signal to noise ratio. Furthermore, because the accelerometer is mounted on a known axis along the penis, it can be used as an inclinometer to detect the orientation of the penis. If the penis is erect, the accelerometer will detect gravity along a certain axis and in a certain direction. This makes it possible to detect erections even though no penis housing is used. A strain gauge could be placed on the glans ring 1102 to achieve the same type of erection detection; or, the force sensor method could be integrated for erection detection, but would require a hard glans ring and would increase its size. Therefore the accelerometer-based erection sensing mechanism described is superior to the alternatives. It allows the glans ring 1102 to be compact and flexible, and does not require complex geometries, strain gauges or other expensive components. The glans ring 1102 also includes an infrared diode and a photocoupler, and an electrical contact, and, through the methods already presented detects the presence of the penis. Due to the different optical reflectance/transmittance characteristics of the frenum area and the area of the shaft of the penis, and the different total resistance measured between 406 and 1104 it is even possible to detect when the glans ring 1102 is properly mounted near the glans as opposed to simply placed along the shaft of the penis near its base. The glans area has thinner skin and as a result the light is strongly refracted. The same concept allows the device to know whether the penis is inserted or whether a finger is inserted. Electrode 408 mounted on the glans ring 1102 is used in conjunction with one of the other electrodes (402 or 404) to administer an aversive current stimulus when a prohibited behavior other than removing the glans ring 1102 is detected. When the glans ring 1102 is removed, 402 and 404 are used to deliver a more aversive electrical stimulus until the glans ring is worn again.

Other modifications and implementations will occur to those skilled in the art without departing from the spirit and the scope of the invention as claimed. Accordingly, the above description is not intended to limit the invention, except as indicated in the following claims.

What is claimed is:

1. A male chastity apparatus configured to be worn on human male genitals having a penis and a scrotal sack containing at least one testicle, the male chastity apparatus comprising:
 a penis cage capable of physically inhibiting tactile access to the penis, the penis cage including at least one pull-out sensor configured to detect a pullout condition, the pullout condition occurring whenever the penis is not inserted into the penis cage: and
 a scrotal ring, configured to be attached and secured only attachable around the scrotal sack of the male genitals above the at least one testicle so as to prevent the at least one testicle from passing through the scrotal ring after the scrotal ring has been attached and secured around the scrotal sack, the scrotal ring having two electrodes configured to apply an electric stimulus to the scrotal sack in response to detection of the pullout condition, the stimulus continuing until the pull-out condition ceases.

2. The apparatus of claim 1, wherein the at least one pull-out sensor is one of:
 a current change sensor;
 a resistance change sensor;
 a temperature change sensor;
 an optical sensor;
 an infra-red sensor;
 a pressure change sensor;
 a capacitive sensor;
 an ultra-sonic sensor;
 a force sensing resistor a strain gauge;
 a thermistor; and
 a piezoelectric sensor.

* * * * *